US012606515B2

(12) United States Patent
Wada et al.

(10) Patent No.: US 12,606,515 B2
(45) Date of Patent: Apr. 21, 2026

(54) METHOD FOR PRODUCING COMPOUND

(71) Applicant: NIPPON SHOKUBAI CO., LTD.,
Osaka (JP)

(72) Inventors: Hiroki Wada, Himeji (JP); Masashi Mukae, Himeji (JP); Yasutaka Takemoto, Himeji (JP); Toyofumi Sakai, Himeji (JP)

(73) Assignee: NIPPON SHOKUBAI CO., LTD.,
Osaka (JP)

( * ) Notice: Subject to any disclaimer, the term of this patent is extended or adjusted under 35 U.S.C. 154(b) by 508 days.

(21) Appl. No.: 18/025,576

(22) PCT Filed: Sep. 8, 2021

(86) PCT No.: PCT/JP2021/033037
§ 371 (c)(1),
(2) Date: Mar. 10, 2023

(87) PCT Pub. No.: WO2022/054841
PCT Pub. Date: Mar. 17, 2022

(65) Prior Publication Data
US 2024/0025835 A1 Jan. 25, 2024

(30) Foreign Application Priority Data

Sep. 11, 2020 (JP) ................................. 2020-153287

(51) Int. Cl.
*C07C 51/43* (2006.01)
*B01D 9/00* (2006.01)
(52) U.S. Cl.
CPC ............ *C07C 51/43* (2013.01); *B01D 9/0045* (2013.01); *B01D 9/0059* (2013.01); *B01D 2009/0086* (2013.01)

(58) Field of Classification Search
CPC .... C07C 51/43; B01D 9/0045; B01D 9/0059; B01D 2009/0086
See application file for complete search history.

(56) References Cited

U.S. PATENT DOCUMENTS 4,286,101 A * 8/1981 Hashizume ........... C07C 51/265
562/487
6,018,077 A * 1/2000 Ohkoshi ............... C07C 51/265
562/414

(Continued)

FOREIGN PATENT DOCUMENTS

JP 11-123302 A 5/1999
JP H11123302 A 5/1999

(Continued)

OTHER PUBLICATIONS

Verdoes et al., Speciality Chemicals Magazine, 2009.

(Continued)

*Primary Examiner* — Robert M Kunemund
(74) *Attorney, Agent, or Firm* — Dickinson Wright PLLC

(57) ABSTRACT

The present invention provides a method capable of sufficiently reducing impurities with excellent separation efficiency even from a crystal-containing slurry that contains a low-purity mother liquor and has poor solid-liquid separation properties. The present invention relates to a method for producing a compound, the method including: a step of feeding a slurry containing crystals of the compound to a hydraulic wash column; a step of melting crystals in a crystal-containing circulation slurry discharged from the hydraulic wash column; and a step of returning a portion of a circulation liquid containing a melt obtained in the melting step to the hydraulic wash column, wherein the circulation liquid returned in the returning step in an amount of more (Continued)

than 30% by mass relative to 100% by mass of the melt serves as a washing liquid for crystals.

12 Claims, 1 Drawing Sheet

(56) References Cited

U.S. PATENT DOCUMENTS

| | | | | |
|---|---|---|---|---|
| 7,812,206 | B2 * | 10/2010 | Wilsak ................. | B01D 29/114 |
| | | | | 585/812 |
| 8,232,425 | B2 * | 7/2012 | Dieterle .................. | C07C 51/43 |
| | | | | 562/598 |
| 10,919,834 | B2 * | 2/2021 | Kase ........................ | C07C 57/04 |
| 2002/0008064 | A1 | 1/2002 | Hamamoto et al. | |
| 2003/0060661 | A1 | 3/2003 | Eck et al. | |
| 2003/0175159 | A1 | 9/2003 | Heilek et al. | |
| 2004/0256319 | A1 | 12/2004 | Hammon et al. | |
| 2005/0006299 | A1 | 1/2005 | Heilek et al. | |
| 2007/0129572 | A1 | 6/2007 | Shibusawa et al. | |
| 2007/0225539 | A1 | 9/2007 | Wilsak et al. | |
| 2010/0273970 | A1 | 10/2010 | Koestner et al. | |
| 2011/0124834 | A1 | 5/2011 | Heilek et al. | |
| 2020/0181056 | A1 | 6/2020 | Kase et al. | |

FOREIGN PATENT DOCUMENTS

| | | | |
|---|---|---|---|
| JP | 20021017 | A | 1/2002 |
| JP | 2003530376 | A | 10/2003 |
| JP | 2005509009 | A | 4/2005 |
| JP | 2005509010 | A | 4/2005 |
| JP | 2006069959 | A | 3/2006 |
| JP | 2007182437 | A | 7/2007 |
| JP | 2009-530103 | A | 8/2009 |
| JP | 2010059107 | A | 3/2010 |
| JP | 2011-514311 | A | 5/2011 |
| WO | 2007108875 | A1 | 9/2007 |
| WO | 2009095111 | A1 | 8/2009 |
| WO | 2011/045356 | A1 | 4/2011 |
| WO | 2018216699 | A1 | 11/2018 |

OTHER PUBLICATIONS

International Search Report dated Dec. 7, 2021, which issued in the corresponding PCT Patent Application No. PCT/JP2021/033037, including English translation.

* cited by examiner

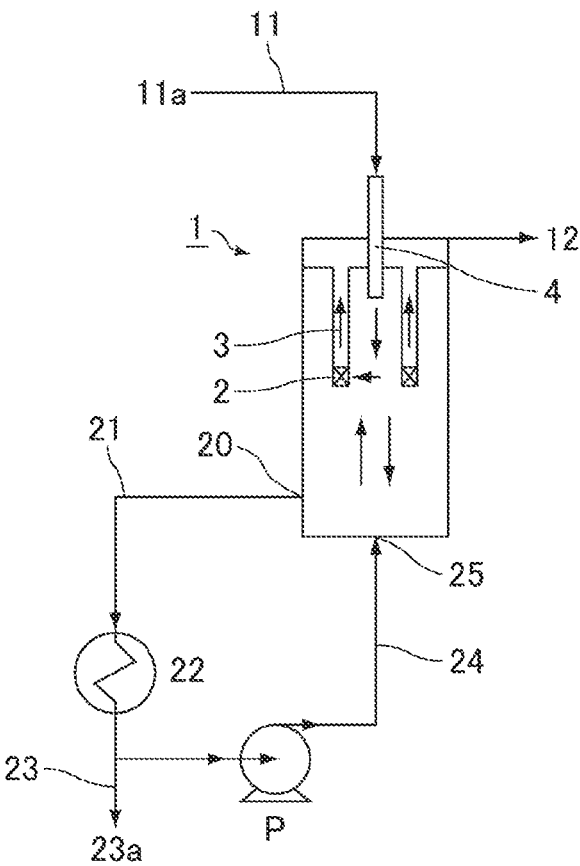

METHOD FOR PRODUCING COMPOUND

TECHNICAL FIELD

The present invention relates to methods for producing compounds. More specifically, the present invention relates to a method for producing a compound, a method for purifying a compound, a purification apparatus, and a mother liquor discharging apparatus for a hydraulic wash column.

BACKGROUND ART

Compounds, including easily polymerizable compounds such as (meth)acrylic acid, are widely used industrially as raw materials for resins, for example. In response, various excellent purification techniques capable of reducing impurities have been investigated.

Industrially, many of crude compounds, which are compounds before purification, are purified through continuous purification processes. Disclosed is a method for producing acrylic acid including: collecting and crystallization purifying a gas containing acrylic acid obtained by catalytic oxidation of a raw material gas in gas phase; and returning acrylic acid obtained by decomposing a substance obtained by Michael addition of acrylic acid in a residual mother liquor to the collecting step, for example (see, for example, Patent Literature 1). This method enables high-yield production of acrylic acid.

In the purification process, a wash column such as a hydraulic wash column (HWC) may be used. Patent Literatures 2 to 4 and Non-Patent Literature 1 disclose conventional purification methods using wash columns.

CITATION LIST

Patent Literature

Patent Literature 1: JP 2007-182437 A
Patent Literature 2: JP 2003-530376 T
Patent Literature 3: JP 2005-509010 T
Patent Literature 4: JP 2005-509009 T

Non-Patent Literature

Non-Patent Literature 1: Verdoes et al., "High purity products by crystallisation", Specialty Chemicals Magazine, September 2009, pp. 32-35

SUMMARY OF INVENTION

Technical Problem

As described above, more excellent purification techniques for producing compounds have been required, and excellent impurity separation efficiency has been desired. The present invention has been made in view of the above-mentioned current state of the art, and aims to provide a method capable of sufficiently reducing impurities with excellent separation efficiency even from a slurry having poor solid-liquid separation properties containing crystals and a low-purity mother liquor.

Solution to Problem

The present inventors have studied methods for producing compounds, and focused on using a hydraulic wash column with high washing efficiency in the purification of compounds. The present inventors have found that excellent separation efficiency can be achieved in the following way: a crystal-containing circulation slurry is discharged from a hydraulic wash column; and a portion of a circulation liquid containing a melt obtained in a step of melting the crystals is returned to the hydraulic wash column so that the circulation liquid in an amount of more than 30% by mass relative to 100% by mass of the melt serves as a washing liquid for crystals. Thereby, the present invention has been achieved.

That is, the present invention relates to a method for producing a compound, the method including: a step of feeding a slurry containing crystals of the compound to a hydraulic wash column; a step of melting crystals in a crystal-containing circulation slurry discharged from the hydraulic wash column; and a step of returning a portion of a circulation liquid containing a melt obtained in the melting step to the hydraulic wash column, wherein the circulation liquid returned in the returning step in an amount of more than 30% by mass relative to 100% by mass of the melt serves as a washing liquid for crystals.

Patent Literatures 2 to 4 and Non-Patent Literature 1 describe wash columns, but Patent Literature 2 and Non-Patent Literature 1 do not disclose that more than 30% by mass of the melt obtained in the melting step is returned to the hydraulic wash column as a washing liquid, and do not disclose that a larger amount of the washing liquid achieves excellent impurity separation efficiency even when the slurry to be purified contains a low-purity mother liquor. Patent Literatures 3 and 4 do not describe the amount of washing liquid at all.

Advantageous Effects of Invention

The production method of the present invention achieves excellent impurity separation efficiency.

BRIEF DESCRIPTION OF DRAWINGS

FIG. 1 is an exemplary schematic diagram of a purification apparatus according to a production method of the present invention.

DESCRIPTION OF EMBODIMENTS

The present invention will be described in detail below.

It should be noted that combinations of two or more of the preferred features of the present invention described below are also preferred embodiments of the present invention.

The following first describes a method for producing a compound of the present invention, followed by descriptions of a method for purifying a compound of the present invention, a purification apparatus of the present invention, and a mother liquor discharging apparatus for a hydraulic wash column of the present invention in this order.

Method for Producing Compound of the Present Invention

The method for producing a compound of the present invention includes a step of feeding a slurry containing crystals of the compound to a hydraulic wash column; a step of melting crystals in a crystal-containing circulation slurry discharged from the hydraulic wash column; and a step of returning a portion of a circulation liquid containing a melt obtained in the melting step to the hydraulic wash column, wherein the circulation liquid returned in the returning step in an amount of more than 30% by mass relative to 100% by mass of the melt serves as a washing liquid for crystals.

Basically, an object to be purified is subjected to the feeding step, the melting step, and the returning step in this order. For example, as shown in FIG. 1, a crystal-containing slurry 11a is fed into a hydraulic wash column 1 through a feed line 11 and a pipe 4; a crystal-containing circulation slurry is discharged through a circulation slurry discharging port 20 at the bottom of the hydraulic wash column 1 and passes through a discharging line 21 that connects the circulation slurry discharging port 20 and a melting unit 22; and the crystals in the circulation slurry are melted in the unit 22. A portion of a circulation liquid containing a melt obtained by melting the crystals in the melting unit 22 is returned into the hydraulic wash column 1 through a return line 24 that connects the melting unit 22 and a return port 25. The rest of the circulation liquid passes through a product discharging line 23 branched from the return line 24 and is discharged from the purification apparatus as a product 23a. The following first describes the returning step, followed by descriptions of the feeding step, the melting step, and other steps in this order. In a continuous purification process, the steps are usually performed simultaneously in the view of the whole purification apparatus.

Herein, the term "compound" refers to a compound obtained by the production method of the present invention, and does not refer to raw materials, by-products, and solvents in the production method of the present invention. The term "compound" may also be referred to as a "target compound" or a "target object". Herein, the term "impurity/impurities" refer to components other than the "compound", such as raw materials, by-products, and solvents.

Returning Step

The returning step includes returning a portion of a circulation liquid containing a melt obtained in the melting step to the hydraulic wash column, wherein the circulation liquid returned in the returning step in an amount of more than 30% by mass relative to 100% by mass of the melt serves as a washing liquid for crystals. Herein, the percentage by mass of the washing liquid for crystals relative to 100% by mass of the melt is also referred to as a return percentage. The melt is contained in the circulation liquid and thus cannot be separated as the melt.

The circulation liquid contains the melt obtained in the melting step. In other words, the crystals in the discharged circulation slurry are melted to be a melt, so that the suspended circulation slurry becomes a non-suspended circulation liquid.

The circulation liquid is circulated as follows: the circulation liquid is discharged in the form of crystal-containing circulation slurry from the hydraulic wash column; and a portion of the circulation liquid containing the melt obtained in the melting step is returned to the hydraulic wash column and passes through the hydraulic wash column for circulation. In other words, the circulation liquid flows in a circulation path that passes through the hydraulic wash column. Herein, the liquid component in the circulation slurry flowing in the circulation path is also referred to as a circulation liquid.

The melt obtained in the melting step refers to a liquid obtained by melting the crystals in the circulation slurry discharged from the hydraulic wash column in the melting step. The melt does not include those derived from the circulation liquid (liquid components) in the circulation slurry.

Here, the circulation slurry is a suspension of crystals of the compound and the circulation liquid, and flows in the circulation path.

The circulation path is a path that circulates through the hydraulic wash column. A specific example thereof is a circulation path including: a discharging line that connects the circulation slurry discharging port of the hydraulic wash column and the melting unit; and a return line that connects the melting unit and the return port of the hydraulic wash column. The circulation slurry or the circulation liquid containing the melt is circulated in the circulation path. Herein, the circulation path is also referred to as a melt loop.

In the circulation path, the circulation slurry flows a zone between a point where the circulation liquid is mixed with the crystals in the hydraulic wash column to be a circulation slurry and a point where the crystals in the circulation slurry are melted. For example, in the melt loop, the circulation liquid returned through the return port 25 to the bottom of the hydraulic wash column is mixed with the crystals in the hydraulic wash column to be a circulation slurry, and the circulation slurry flows in a path (the discharging line 21) between the circulation slurry discharging port 20 and the melting unit 22. The circulation liquid to be contained in the circulation slurry substantially consists of a portion of the circulation liquid that is returned to the hydraulic wash column in the returning step, the portion not serving as a washing liquid for crystals but serving as a recirculating liquid.

The washing liquid is a portion of the circulation liquid that is returned to the hydraulic wash column. After returning to the hydraulic wash column, the portion of the circulation liquid is not discharged through the discharging port of the hydraulic wash column and is not recirculated in the circulation path, but, for example, flows countercurrent (preferably in an upward direction) to the conveying direction of the crystals through gaps between crystals of a crystal bed in the hydraulic wash column, thereby washing the crystals in the hydraulic wash column.

As described above, the washing liquid is a portion that is not recirculated in the circulation path, but is separated from the circulation liquid flowing in the circulation path after the circulation liquid is returned to the hydraulic wash column. A product is also discharged to be separated from the circulation liquid flowing in the circulation path. Separately, the crystals are discharged from the hydraulic wash column and introduced into the circulation liquid flowing in the circulation path. The amount removed from the circulation path and the amount introduced into the circulation path are balanced during continuous operation. The sum of the amount of the washing liquid and the amount of the product discharged is equal to the amount of the crystals discharged from the hydraulic wash column, i.e., the amount of the melt obtained in the melting step. This also indicates that the amount of the washing liquid is equal to the amount obtained by subtracting the amount of the discharged product from the amount of the melt of the discharged crystals.

The return percentage in the returning step can be determined as follows: the amount of the crystals fed to the melting step is determined in terms of the flow rate of the slurry fed to the hydraulic wash column and the concentration of the slurry determined from sampling, specific gravity measurement, the freezing point of the mother liquor, and the like, and the flow rate of the circulation liquid discharged as a product is measured with a flow meter. Alternatively, the return percentage can be determined from the impurity concentration in the mother liquor in the slurry fed to the hydraulic wash column (hereinafter also referred to as a feed slurry), the impurity concentration in the discharged mother liquor, and the impurity concentration in the discharged product.

The following describes an exemplary method for calculating the return percentage in the returning step. In the following example, for the sake of simplification, the purity of the crystals was assumed to be 100% in calculating the return percentage.

The flow rate of the crystal-containing slurry 11a fed to the hydraulic wash column is measured with a flow meter. For example, the flow rate is 100 kg/h.

A sample of the crystal-containing slurry 11a is analyzed to compare the purity of the mother liquor before melting of the crystals, 94.4% to the purity of the liquid after melting the crystals of 95.0%. Thereby, the slurry concentration is calculated to be 10% by mass.

Alternatively, it is assumed that the specific gravity of the crystal-containing slurry 11a is measured to be 1.07. The specific gravity of the liquid is 1.05 and the specific gravity of the crystal is 1.25. Thus, the slurry concentration is calculated to be 10% by mass.

Here, it is assumed that the amount of crystals in the crystal-containing slurry 11a is equal to the amount of crystals in the circulation slurry. The circulation slurry may be used to directly calculate the amount of the crystals in a similar manner.

Thus, the amount of the crystals in the circulation slurry is determined to be 10 kg/h (=100 kg/h×10% by mass).

The flow rate of the product 23a is measured with a flow meter to be 6.0 kg/h.

The amount of the washing liquid is equal to the amount obtained by subtracting the amount of the discharged product from the amount of the melt (the amount of the crystals in the circulation slurry), which is represented by 10−6.0=4.0 kg/h. The return percentage is 40% (=4.0/10× 100%) obtained by dividing the amount of the washing liquid by the amount of the melt of the discharged crystals.

In the returning step, as described above, a portion of the circulation liquid containing the melt obtained in the melting step is returned to the hydraulic wash column, and the circulation liquid returned in the returning step in an amount of more than 30% by mass relative to 100% by mass of the melt serves as a washing liquid for crystals. The circulation liquid is preferably returned such that it flows countercurrent to the conveying direction of the crystals (bed). The direction may be appropriately determined depending on the specific gravities of the washing liquid and the crystals. For example, when the specific gravity of the crystals is greater than the specific gravity of the mother liquor, the circulation liquid is preferably returned such that it flows in an upward direction. The term "upward direction" preferably refers to a substantially vertically upward direction with respect to the horizontal plane. Thus, the crystals can be washed efficiently.

The return percentage in the returning step is more than 30% by mass, preferably 31% by mass or more, more preferably 35% by mass or more, still more preferably 40% by mass or more relative to 100% by mass of the melt obtained in the melting step.

The return percentage is preferably 80% by mass or less, more preferably 75% by mass or less, still more preferably 70% by mass or less.

In an industrial-scale hydraulic wash column, in discharging a product accompanying the returning step, the product is discharged at a rate of 5 kg/h to $4.0×10^4$ kg/h.

In the production method of the present invention, the outer wall surface of the hydraulic wash column is preferably heated.

In the production method of the present invention, a larger amount of the washing liquid returns in the returning step than in conventional methods, and thus, the purity of the compound in the mother liquor that is fed to the hydraulic wash column and discharged through the filter is high. As a result, the freezing point of the mother liquor increases, leading to a concern of clogging of pipes due to freezing. In particular, when the crystal-containing slurry is filtered with a filter as described later, clogging of the filter due to freezing is concerned. Also concerned is, for example, a reduction in the amount to be treated due to lowering of the conveying force of the crystal bed caused by freezing of the washing liquid and mother liquor passing near the wall surface. Such freezing can be prevented by heating the outer wall surface of the hydraulic wash column, leading to stable production of the compound.

The outer wall surface of the hydraulic wash column is preferably heated by a heating medium.

The heating medium may be any liquid or gas, and examples include water, antifreeze, a methanol water mixture (an aqueous methanol solution), and gas. The heating medium may be appropriately selected in consideration of the freezing point of the compound to be purified and the like.

The flow rate of the heating medium may be appropriately selected so that the difference between the inlet temperature and the outlet temperature of the heating medium is less than 5° C., preferably less than 3° C., more preferably less than 1° C.

In the production method of the present invention, the outer wall surface of the hydraulic wash column is preferably heated by a heating medium having a temperature higher than the melting point of the compound by at least 3° C.

As described above, the temperature of the heating medium is preferably higher than the melting point of the compound by 3° C. or more, more preferably by 5° C. or more, still more preferably by 7° C. or more.

The temperature of the heating medium is preferably higher than the melting point of the compound by not more than 30° C., more preferably by not more than 20° C. In other words, the temperature of the heating medium is usually higher than the melting point of the compound, and the difference therebetween is preferably not more than 30° C., more preferably not more than 20° C. The melting point of the compound is the melting point of a target compound and is preferably 0° C. to 80° C., more preferably 1° C. to 50° C., still more preferably 3° C. to 40° C., particularly preferably 5° C. to 20° C.

The heating may be performed by heating part of the hydraulic wash column with a heating medium or the like. Preferably, substantially the entire hydraulic wash column is heated (jacket heating).

In the jacket heating, when the heating medium is liquid, the heating medium is preferably fed from a lower part of a jacket. In this case, the temperature of the heating medium preferably refers to the inlet temperature.

The heating medium may be fed from an upper part of the jacket. In this case, the temperature of the heating medium preferably refers to the outlet temperature.

During operation, the inside of the hydraulic wash column is basically under pressure. The pressure is preferably within the range of 0.05 to 1.0 MPa.

Feeding Step

In the feeding step, the slurry containing crystals of the compound is fed to the hydraulic wash column. The crystal-containing slurry is a suspension of crystals of the compound and a mother liquor. In other words, the liquid portion of the slurry containing crystals of the compound to be fed to the hydraulic wash column is the mother liquor. The crystal-containing slurry can be obtained by generating crystals in a compound-containing solution (e.g., a (meth) acrylic acid aqueous solution or a crude (meth)acrylic acid solution) as described later. The compound-containing solution may be prepared in-house or procured from outside sources. The compound-containing solution encompasses a crude compound.

The mass percentage of the crystals in the crystal-containing slurry to be fed to the hydraulic wash column is preferably 1% by mass or more, more preferably 3% by mass or more, still more preferably 5% by mass or more.

The mass percentage of the crystals is preferably 50% by mass or less, more preferably 40% by mass or less, still more preferably 30% by mass or less, particularly preferably 20% by mass or less.

Herein, the expression "crystal-containing slurry to be fed to the hydraulic wash column" refers to the crystal-containing slurry immediately before being fed to the hydraulic wash column.

Preferably, in the crystal-containing slurry to be fed to the hydraulic wash column, the mother liquor contains the compound. Examples of the mother liquor include the above-described compound and an aqueous solution of the compound. The mother liquor usually contains impurities other than the compound and water.

In the method for producing a compound of the present invention, the purity (mass percentage) of the compound in the mother liquor in the crystal-containing slurry to be fed to the hydraulic wash column is preferably 97% by mass or less. Thereby, the effect of the present invention can be significantly achieved.

More preferably, the mass percentage of the compound in the mother liquor is 96% by mass or less.

The mass percentage of the compound in the mother liquor is preferably 85% by mass or more, more preferably 88% by mass or more, still more preferably 90% by mass or more.

In the production method of the present invention, the compound preferably has a melting point of 0° C. to 80° C., more preferably 1° C. to 50° C., still more preferably 3° C. to 40° C., particularly preferably 5° C. to 20° C., as described above.

The compound having a melting point within the above range is preferably an easily polymerizable compound having a reactive double bond.

In particular, in the production method of the present invention, the compound is more preferably an unsaturated carboxylic acid, still more preferably (meth)acrylic acid, particularly preferably acrylic acid. Herein, the term "(meth) acrylic acid" refers to acrylic acid and/or methacrylic acid.

The mass percentage of water in the mother liquor is preferably 0.1% by mass or more, more preferably 0.5% by mass or more, still more preferably 1% by mass or more.

The mass percentage of water in the mother liquor is preferably 8% by mass or less, more preferably 6% by mass or less, still more preferably 4% by mass or less.

The mass percentage of impurities other than the compound and water in the mother liquor is preferably 0.1% by mass or more, more preferably 0.4% by mass or more, still more preferably 0.8% by mass or more, in order to make the effect of the invention significant.

The mass percentage of impurities other than the compound and water in the mother liquor is preferably 8% by mass or less, more preferably 6% by mass or less, still more preferably 4% by mass or less.

When the compound is (meth)acrylic acid, the impurities other than the compound and water may include acetic acid and furfural, for example.

In this case, the mass percentage of acetic acid in the mother liquor is preferably 0.1% by mass or more, more preferably 0.3% by mass or more, still more preferably 0.7% by mass or more, in order to make the effect of the invention significant.

The mass percentage of acetic acid in the mother liquor is preferably 8% by mass or less, more preferably 6% by mass or less, still more preferably 4% by mass or less.

When the compound is (meth)acrylic acid, the mass percentage of furfural in the mother liquor is more preferably 0.01% by mass or more, more preferably 0.05% by mass or more, still more preferably 0.1% by mass or more, in order to make the effect of the invention significant.

The mass percentage of furfural in the mother liquor is preferably 2% by mass or less, more preferably 1% by mass or less, still more preferably 0.5% by mass or less.

In the feeding step, the crystal-containing slurry may be fed at any feed rate. For example, the feed rate is $0.2 \times 10^3$ to $4.0 \times 10^5$ kg/h in an industrial-scale hydraulic wash column.

In the feeding step, the feed temperature of the crystal-containing slurry can be appropriately selected according to the melting point of the compound or the like. For example, the feed temperature can be appropriately adjusted within the range of 0° C. to 80° C.

For example, when the compound is (meth)acrylic acid, the feed temperature of the crystal-containing slurry is preferably 5° C. to 13° C., more preferably 6° C. to 12° C.

The feed temperature of the crystal-containing slurry is the temperature of the mother liquor in the crystal-containing slurry immediately before being fed to the hydraulic wash column.

Melting Step

In the melting step, the crystals in the crystal-containing circulation slurry discharged from the hydraulic wash column are melted.

The crystals originate from a crystal bed formed at the bottom of the hydraulic wash column. The crystals can be discharged using the below-described mechanism that discharges the crystals from the crystal bed in the hydraulic wash column.

The crystals are usually discharged together with the circulation liquid, i.e., the crystals are discharged in the form of a crystal-containing circulation slurry. This circulation slurry is subjected to the melting step.

The mass percentage of the crystals in the crystal-containing circulation slurry discharged from the hydraulic wash column is preferably 0.5% by mass or more, more preferably 1% by mass or more, still more preferably 3% by mass or more, particularly preferably 5% by mass or more.

The mass percentage of the crystals is preferably 40% by mass or less, more preferably 30% by mass or less, still more preferably 20% by mass or less, particularly preferably 10% by mass or less.

Herein, the crystal-containing circulation slurry or crystals discharged from the hydraulic wash column refer(s) to the crystal-containing circulation slurry or crystals immediately after being discharged from the hydraulic wash column, and, for example, refer(s) to the crystal-containing circulation slurry or crystals in the discharging line (pipe) that connects the circulation slurry discharging port and the melting unit.

The crystal-containing circulation slurry is discharged from the hydraulic wash column at a discharging rate of $2 \times 10^3$ to $5 \times 10^5$ kg/h in an industrial-scale hydraulic wash column, for example, but is not limited thereto.

The discharged crystals can be melted using a heater. Examples of the heater include those having a structure that efficiently transfers heat to the crystal-containing slurry, such as a vertical multitubular heat exchanger, a horizontal multitubular heat exchanger, a double pipe heat exchanger, a spiral heat exchanger, a plate heat exchanger, or an electric heater. Preferably, the heater is provided in the melt loop and the circulation slurry and the circulation liquid after the melting step are circulated in the forced circulation system in which the circulation slurry is circulated by a pump provided in the melt loop.

The heating temperature in the melting step may be appropriately selected according to the melting point of the compound, and can be adjusted within the range of 10° C. to 100° C., for example.

For example, when the compound is (meth)acrylic acid, the heating temperature in the melting step is preferably 15° C. or higher, more preferably 18° C. or higher. The heating temperature is preferably 50° C. or lower, more preferably 40° C. or lower.

When the heating is performed by feeding a heating medium to the melting unit, the heating temperature in the melting step is the temperature of the heating medium.

The temperature of the circulation liquid containing the melt at the outlet of the melting step (the melting unit) is preferably set to a temperature 1° C. to 10° C. higher than the melting point of the circulation liquid containing the melt obtained in the melting step (e.g., the circulation liquid containing the melt obtained after the crystal-containing slurry passes through the heat exchanger or the like and the crystals are melted).

The melting time in the melting step may be appropriately selected to the extent that the crystals are sufficiently melted.

Mother Liquor Discharging Step

The production method of the present invention preferably further includes a step of discharging a mother liquor, the step including filtering the crystal-containing slurry in the hydraulic wash column with a filter and discharging the mother liquor through a pipe connected to the filter. Preferably, in the mother liquor discharging step, a portion of the washing liquid is discharged together with the mother liquor. Thus, the discharged mother liquor preferably contains a portion of the washing liquid.

The discharged mother liquor can be recycled and reused. For example, reuse of the discharged mother liquor at least as a portion of the crystal-containing slurry to be fed to the hydraulic wash column can provide a compound with further improved quality.

When the specific gravity of the crystals is higher than that of the mother liquor, the mother liquor in the slurry fed in the feeding step flows downward from the top, runs into the washing liquid flowing upward from the bottom, and is pushed back. Thereby, the mother liquor is discharged through the filter.

In the production method of the present invention, the thermal conductivity of the filter is preferably different from the thermal conductivity of the pipe.

For example, the thermal conductivity of the filter is preferably lower than the thermal conductivity of the pipe. This can prevent cooling of the filter connected to the pipe having a relatively low temperature and extending in an upper part of the hydraulic wash column, and can sufficiently prevent clogging of the filter due to freezing of the mother liquor. For example, since the production method of the present invention uses a large amount of washing liquid, the purity of the mother liquor discharged through the filter is high and the freezing point of the mother liquor near the filter is high. When this freezing point is higher than the temperature of the crystal-containing slurry located above the filter, where the temperature is relatively low, the filter is cooled through the pipe that extends in an upper part of the hydraulic wash column. This leads to a concern about clogging of the filter due to freezing of the mother liquor. The production method of the present invention can sufficiently prevent such clogging.

The thermal conductivity of the filter is preferably lower than the thermal conductivity of the pipe by 1 W/(m·K) or more, more preferably by 5 W/(m·K) or more, still more preferably by 15 W/(m·K) or more, for example.

The thermal conductivity of the filter is preferably lower than the thermal conductivity of the pipe by not more than 30 W/(m·K), more preferably by not more than 25 W/(m·K), still more preferably by not more than 20 W/(m·K). In other words, the thermal conductivity of the filter is usually lower than the thermal conductivity of the pipe, and the difference therebetween is preferably not more than 30 W/(m·K), more preferably not more than 25 W/(m·K), still more preferably not more than 20 W/(m·K).

The thermal conductivity of the filter is preferably 20 W/(m·K) or lower, more preferably 10 W/(m·K) or lower, still more preferably 1 W/(m·K) or lower.

The lower limit of the thermal conductivity of the filter is usually 0.1 W/(m·K) or higher, but is not limited thereto.

The material of the filter is preferably different from the material of the pipe.

For example, the filter may be made of any material and may be made of, for example, metal such as stainless steel or resin such as polytetrafluoroethylene (PTFE), polyetheretherketone (PEEK), a tetrafluoroethylene-perfluoroalkylvinyl ether copolymer (PFA), or polyetherketone (PEK), with the latter being preferred. The pipe may be made of any material and is preferably made of metal or an alloy.

In particular, preferably, the ratio of the thermal conductivity of the pipe to the thermal conductivity of the filter is 10 to 100.

The ratio is more preferably 15 to 80, still more preferably 50 to 75.

Thus, the production method of the present invention can stably produce a compound.

The mother liquor discharged in the mother liquor discharging step usually contains the compound. Examples of the mother liquor include a melt of the compound and an aqueous solution of the compound. The mother liquor usually contains impurities other than the compound and water.

The mother liquor discharged in the mother liquor discharging step refers to the mother liquor immediately after passing through the filter in the mother liquor discharging step.

The mother liquor discharging step can be appropriately performed using a pump or the like.

Step of Preparing Crystal-Containing Slurry

The production method of the present invention preferably further includes a step of preparing a slurry containing crystals of a compound from a compound-containing solution.

The compound-containing solution can be prepared by collecting the gas of a compound, which is a reaction product obtained by a reactor, in an absorption tower, for example. The compound-containing solution encompasses a crude compound obtained by purifying the collected compound. The compound-containing solution is not limited to one synthesized in-house, and may be one procured from outside sources.

The compound-containing solution is cooled, for example, and thereby the slurry containing crystals of the compound can be obtained.

The compound-containing solution contains impurities other than the compound and water.

In the production method of the present invention, the compound-containing solution is preferably a (meth)acrylic acid aqueous solution or a crude (meth)acrylic acid solution.

The (meth)acrylic acid aqueous solution refers to a solution in which (meth)acrylic acid is dissolved in water. The crude (meth)acrylic acid solution is a solution composed of (meth)acrylic acid and containing impurities such as by-products produced during the production of the (meth) acrylic acid.

Examples of the impurities include acids such as propionic acid, acetic acid, maleic acid, benzoic acid, and acrylic acid dimers; aldehydes such as acrolein, furfural, formaldehyde, and glyoxal; methyl isobutyl ketone; toluene; protoanemonin; and acetone.

The production method of the present invention can sufficiently remove the impurities in the compound-containing solution.

Step of Preparing Compound-Containing Solution

The production method of the present invention preferably further includes a step of preparing the compound-containing solution from a raw material.

The step of preparing the compound-containing solution may be any step that can provide the compound-containing solution. When the compound is (meth)acrylic acid, the step can be suitably carried out by synthesizing acrylic acid, collecting the acrylic acid, and the like, as described in JP 2007-182437 A (Patent Literature 1), for example.

In the method for producing a compound of the present invention, the raw material is preferably at least one selected from the group consisting of propane, propylene, acrolein, isobutene, methacrolein, acetic acid, lactic acid, isopropanol, 1,3-propanediol, glycerol, and 3-hydroxypropionic acid. The (meth)acrylic acid and/or the raw material may also be bio-based (meth)acrylic acids derived from renewable raw materials.

In the step of preparing the compound-containing solution, impurities such as by-products are basically generated. For example, when the compound is (meth)acrylic acid, the impurities generated include water; acids such as propionic acid, acetic acid, maleic acid, benzoic acid, and acrylic acid dimers; aldehydes such as acrolein, furfural, formaldehyde, and glyoxal; methyl isobutyl ketone; toluene; protoanemonin; or acetone. Such impurities can be efficiently separated by purification using the hydraulic wash column in the production method of the present invention. Thereby, a product can be efficiently obtained.

Method for Purifying Compound

The present invention also relates to a method for purifying a compound, the method including: a step of feeding a slurry containing crystals of the compound to a hydraulic wash column; a step of melting crystals in a crystal-containing circulation slurry discharged from the hydraulic wash column; and a step of returning a portion of a circulation liquid containing a melt obtained in the melting step to the hydraulic wash column, wherein the circulation liquid returned in the returning step in an amount of more than 30% by mass relative to 100% by mass of the melt serves as a washing liquid for crystals.

The purification method of the present invention can efficiently purify the crystal-containing slurry.

Preferred embodiments of the purification method of the present invention are the same as the preferred embodiments of the production method of the present invention described above.

Purification Apparatus

The present invention also relates to a purification apparatus that purifies crystals, the purification apparatus including: a hydraulic wash column that includes a discharging port for a crystal-containing circulation slurry and a return port for a circulation liquid containing a melt of discharged crystals; a pipe that feeds a crystal-containing slurry to the hydraulic wash column; a filter that filters the crystal-containing slurry in the hydraulic wash column; a pipe that is connected to the filter and discharges a mother liquor; a unit that melts crystals in a circulation slurry discharged through the discharging port; a mechanism that returns a portion of a circulation liquid containing a melt obtained in the unit that melts crystals to the hydraulic wash column so that at least a portion of the returned circulation liquid serves as a washing liquid for crystals; and a mechanism that controls an amount of the circulation liquid to be returned, wherein a thermal conductivity of the filter is different from a thermal conductivity of the pipe that is connected to the filter and discharges a mother liquor.

The purification apparatus of the present invention includes the mechanism (return mechanism) that returns a portion of the circulation liquid containing the melt obtained in the unit that melts the crystals to the hydraulic wash column. Thus, the purification apparatus of the present invention achieves excellent washing efficiency.

The return mechanism may be any mechanism that is used to return a portion of the circulation liquid separated from the other portion of the circulation liquid to the hydraulic wash column. For example, when the product discharging line that is connected to a product discharging port is branched from the return line that connects the melting unit and the return port, this branched line portion corresponds to the return mechanism. For example, the branched line portion may be a T-junction.

The return port is preferably provided at the bottom of the hydraulic wash column so that the circulation liquid can be returned upward. The return mechanism may be, for example, a combination of the branched line portion and the return port at the bottom of the hydraulic wash column.

The purification apparatus of the present invention further includes the mechanism that controls the amount of the circulation liquid to be returned.

The purification apparatus of the present invention further including the mechanism that controls the amount of the circulation liquid to be returned (control mechanism) can adjust the amount of the circulation liquid to be returned, and if needed, can efficiently separate impurities. Thereby, a product can be efficiently obtained.

An example of the control mechanism is a valve installed in the line of the return mechanism (branched line portion).

The control mechanism may directly or indirectly control the amount of the circulation liquid to be returned.

When the control mechanism directly controls the amount of the circulation liquid to be returned, the control mechanism may be a valve (not shown) installed in the return line 24 shown in FIG. 1, for example.

When the control mechanism indirectly controls the amount of the circulation liquid to be returned, the control mechanism may be a valve (not shown) installed in the product discharging line 23 that is connected to the product discharging port (not shown), for example. The amount of the circulation liquid to be returned through the return line 24 can be controlled resultantly by adjusting the valve installed in the product discharging line 23.

A valve may be installed in both the product discharging line 23 and the return line 24.

For example, the valves can be controlled according to the flow rates in the product discharging line 23 and the return line 24. Furthermore, the valves may be controlled according to the temperature in the hydraulic wash column measured with a multi-point thermometer installed therein.

The hydraulic wash column in the purification apparatus of the present invention may have any dimensions. Preferably, the inner diameter of the column (the crystallization chamber) is 30 to 2000 mm, for example. The height of the column is preferably 1000 to 15000 mm.

The filter that filters the crystal-containing slurry in the hydraulic wash column in the present invention may have any dimensions. Preferably, the inner diameter of the filter is 10 to 30 mm, for example. The height of the filter is preferably 20 to 300 mm.

The filter may be provided with a large number of circular holes, slits (notches), or rectangular holes, for example. The filter may have the same shape as the pipe, such as a cylindrical shape, but is not limited thereto.

When the filter is provided with circular holes, the diameter of each hole may be appropriately adjusted depending on the size of the crystals, and is preferably 50 to 500 μm, for example. The number of holes is not limited, and may be adjusted according to the pressure loss, for example.

The pipe that is connected to the filter and discharges a mother liquor is usually located above the filter.

The number of pipes that are connected to the filter and discharge a mother liquor is not limited. For example, in an industrial-scale hydraulic wash column, preferably, 50 to 350 pipes are connected in parallel per square meter of the cross-sectional area of the hydraulic wash column.

In the purification apparatus of the present invention, preferably, the thermal conductivity of the filter is different from the thermal conductivity of the pipe that is connected to the filter and discharges a mother liquor.

Preferred embodiments of the filter and the pipe that is connected to the filter and discharges a mother liquor are as described for the production method of the present invention.

For example, in the purification apparatus of the present invention, the ratio of the thermal conductivity of the pipe that is connected to the filter and discharges a mother liquor to the thermal conductivity of the filter is preferably 10 to 100.

The purification apparatus of the present invention preferably includes a mechanism that discharges crystals from a crystal bed in the hydraulic wash column.

Non-limiting examples of the mechanism that discharges crystals from a crystal bed include a rotor blade or scraper described in JP 2005-509009 T (Patent Literature 4) and a mechanism using liquid dynamic pressure described in EP 1469926. One or more of these may be used. When the rotor blade or scraper is used, the rotation speed is preferably 20 to 60 rpm. The material of the rotor blade or scraper is preferably metal such as stainless steel.

The purification apparatus of the present invention preferably further includes a mechanism that heats an outer wall surface of the hydraulic wash column.

When the purity of the compound in the mother liquid in the hydraulic wash column increases and the freezing point of the mother liquor increases as a result of, for example, returning a large amount of washing liquid to the hydraulic wash column, clogging of the pipe due to freezing of the mother liquor is concerned. When the crystal-containing slurry in the hydraulic wash column is filtered with a filter, clogging of the filter due to freezing is concerned. Also concerned is a reduction in the amount to be treated caused by lowering of the conveying force of the crystal bed due to freezing of the washing liquid and mother liquor passing near the wall surface. The purification apparatus of the present invention further including a mechanism that heats the outer wall surface of the hydraulic wash column can heat the outer wall surface of the hydraulic wash column, thereby preventing freezing. Thus, the purification apparatus can be stably operated.

Non-limiting examples of the mechanism that heats the outer wall surface of the hydraulic wash column include a heating medium, a steam tracing system, an electric tracing system, and a known heater that adjusts the environmental temperature of the column. For example, part of the hydraulic wash column may be heated with a heating medium or the like, and substantially the entire hydraulic wash column is preferably heated (jacket heating).

When the heating mechanism is of jacket heating, for example, the jacket may be made of any material such as metal (e.g., stainless steel or carbon steel) or resin.

The outside of the jacket may be provided with a heat insulating material, a tracing system, and the like.

The structure of the jacket is not limited.

The inside of the jacket may be provided with any structure such as a structure that promotes heat transfer, such as a baffle.

The jacket preferably has an average thickness (the width of the space where the heating medium flows) of 5 to 200 mm, for example.

The heat flux through the wall of the hydraulic wash column from the jacket is preferably more than 100 $W/m^2$, more preferably more than 200 $W/m^2$, still more preferably more than 500 $W/m^2$.

The upper limit of the heat flux through the wall of the hydraulic wash column from the jacket is usually 4000 $W/m^2$ or less, but is not limited thereto.

A side wall of the jacket may be provided with a sight glass (an observation window) or a hand hole (a hole for putting a hand inside during maintenance). In these cases, they can be covered with a cover. The numbers of sight glasses and hand holes to be provided are not limited.

As described above, non-limiting examples of the heating medium include water, antifreeze, a methanol water mixture (an aqueous methanol solution), and gas. The heating medium may be appropriately selected in consideration of the freezing point of the compound to be purified and the like.

The flow rate of the heating medium may be appropriately selected so that the difference between the inlet temperature and the outlet temperature of the heating medium in the heating mechanism is less than 5° C., preferably less than 3° C., more preferably less than 1° C.

The number of pipes that feed the crystal-containing slurry to the hydraulic wash column and the number of feed nozzles (slurry feed ports) that may be connected to the tips of the pipes are not limited. Each of the numbers may be one or more (FIG. 1 shows the case where the number of pipes that feed the crystal-containing slurry to the hydraulic wash column is one).

The feed nozzle may have, at its tip, a distribution mechanism that distributes the slurry.

The hydraulic wash column may further include a distribution chamber and a central displacer body (see JP 2005-509010 T (Patent Literature 3)).

The purification apparatus of the present invention may further include a dummy pipe that is connected to the filter that filters the crystal-containing slurry in the hydraulic wash column.

The dummy pipe is usually located below the filter. The dummy pipe may be made of any material. For example, it is preferably made of resin such as polytetrafluoroethylene (PTFE), polyetheretherketone (PEEK), a tetrafluoroethylene-perfluoroalkylvinyl ether copolymer (PFA), or polyetherketone (PEK).

The presence of the dummy pipe eliminates a portion where crystals are less likely to accumulate under the filter, resulting in generation of a uniform and solid crystal bed.

The body or the periphery of the hydraulic wash column may be provided with instrumentation equipment such as a thermometer (e.g., a multi-point thermometer), a pressure gauge, or an interface level meter (e.g., an optical interface level meter).

The hydraulic wash column itself may be placed in a temperature-controlled casing (including a large casing such as a building).

As described above, the purification apparatus of the present invention includes the return mechanism and further includes the control mechanism.

Examples of the control mechanism include valves installed in the product discharging line 23 and/or the return line 24. Further, flowmeters may be installed in the feed line 11 (including the pipe 4) that feeds the crystal-containing slurry 11a to the hydraulic wash column, the product discharging line 23, and the return line 24 to measure the flow rates, and the flow rates may be appropriately adjusted by controlling the valves in accordance with the measured flow rates. Furthermore, the valves may be controlled according to the temperature in the hydraulic wash column measured with a multi-point thermometer attached thereto.

Preferably, the purification apparatus of the present invention further includes a product discharging port. For example, more preferably, the purification apparatus of the present invention further includes: the product discharging line branched from the return line that connects the melting unit and the return port; and the product discharging port connected to the product discharging line.

FIG. 1 shows an example of the purification apparatus of the present invention. The crystal-containing slurry 11a is fed into the hydraulic wash column 1 through the feed line 11 (including the pipe 4) that feeds the crystal-containing slurry 11a to the hydraulic wash column, and the crystals deposit at the bottom of the hydraulic wash column 1 to form a crystal bed (not shown). The inside of the hydraulic wash column 1 is provided with filters 2 that filter the crystal-containing slurry in the hydraulic wash column 1 and pipes 3 that are connected to the filters and discharge a mother liquor. Thereby, a mother liquor 12 can be recovered from the crystal-containing slurry and recycled.

The crystals are discharged from the bottom of the hydraulic wash column 1 together with a circulation liquid circulated in a melt loop that passes through the bottom of the hydraulic wash column 1 as a crystal-containing circulation slurry. The circulation slurry passes through the discharging line 21 that connects the circulation slurry discharging port 20 and the melting unit 22 and is sent to the unit 22 that melts the crystals in the circulation slurry. A portion of the circulation liquid containing a melt obtained by melting the crystals in the melting unit 22 is returned into the hydraulic wash column 1 through the return line 24 that connects the melting unit 22 and the return port 25. A portion of the returned circulation liquid serves as a washing liquid for crystals. The rest of the returned circulation liquid is discharged through the circulation slurry discharging port 20 together with the crystals and is recirculated in the melt loop. A portion of the circulation liquid containing the melt obtained by melting the crystals in the melting unit 22 is discharged from the purification apparatus as the purified product 23a through the product discharging line 23 that is branched from the return line 24 and connected to the product discharging port.

Method for Using Purification Apparatus

The present invention also relates to a method for using a purification apparatus including a step of purifying a compound using the purification apparatus of the present invention.

Mother Liquor Discharging Apparatus for
Hydraulic Wash Column

The present invention also relates to a mother liquor discharging apparatus for a hydraulic wash column, the apparatus discharging a mother liquor from the hydraulic wash column, the apparatus including: a filter that filters a crystal-containing slurry in the hydraulic wash column; and a pipe that is connected to the filter and discharges a mother liquor, wherein a thermal conductivity of the filter is different from a thermal conductivity of the pipe that is connected to the filter and discharges a mother liquor.

The mother liquor discharging apparatus for a hydraulic wash column discharges a mother liquor from the hydraulic wash column. In other words, the mother liquor discharging apparatus for a hydraulic wash column separates the mother liquor (and the crystals) from the crystal-containing slurry.

Preferred embodiments of the filter that filters the crystal-containing slurry in the hydraulic wash column and the pipe that is connected to the filter and discharges a mother liquor are as described above for the production method of the present invention.

For example, in the mother liquor discharging apparatus for a hydraulic wash column of the present invention, the ratio of the thermal conductivity of the pipe that is connected to the filter and discharges a mother liquor to the thermal conductivity of the filter is preferably 10 to 100.

Method for Using Mother Liquor Discharging Apparatus

The present invention also relates to a method for using a mother liquor discharging apparatus, the method including a step of purifying a compound using the mother liquor discharging apparatus of the present invention.

EXAMPLES

The present invention will be described in more detail below with reference to examples, but the present invention is not limited by the following examples, and appropriate modifications may be made within the scope that can conform to the gist of the above and later descriptions. All of them are included in the technical scope of the present invention.

Unless otherwise specified, "%" indicates "% by mass" and "parts" indicates "parts by mass."

Measurement Instruments for Gas Chromatography and Liquid Chromatography

Gas chromatograph: GC-2014 available from Shimadzu Corporation

Liquid chromatograph: LC-20AD HPLC unit available from Shimadzu Corporation

These instruments were used for measurement of acetic acid and furfural.

Method for Preparing Acrylic Acid Aqueous Solution

An acrylic acid aqueous solution was prepared according to the method described in WO 2010/032665 as follows: propylene was catalytically oxidized in gas phase to obtain an acrylic acid-containing gas; and the acrylic acid-containing gas was treated in an absorption tower.

Method for Preparing Feed Slurry

The acrylic acid aqueous solution was fed to a crystallization vessel having a heat transfer area of 1.4 m². A cooling medium was fed to a jacket provided around the wall of the crystallization vessel for indirect cooling. Crystals adhering to the inner surface of the crystallization vessel were scraped off with a scraper installed in the crystallization vessel. Thus, a crystal-containing slurry (feed slurry) was prepared.

Purification Apparatus

A purification apparatus used includes the following units and is similar to the purification apparatus shown in FIG. 1, except for the number of filters 2 and the number of mother liquor discharging pipes 3.

Hydraulic wash column 1: inner diameter 60 mm; height 2000 mm

Filter 2: inner diameter 25 mm; length (height) 200 mm; number of filters 1; thermal conductivity 0.25 W/(m·K); material PEEK; structure of the filter includes circular holes with a diameter of 250 μm Pipe 3 that is connected to the filter 2 and discharges a mother liquor: inner diameter 25 mm; length 1600 mm; number of pipes 1; thermal conductivity 16.3 W/(m·K); material stainless steel Ratio of the thermal conductivity of the pipe 3 that discharges a mother liquor to the thermal conductivity of the filter 2: 16.3/0.25=65.2

Return of circulation liquid into the hydraulic wash column 1: upward return from the bottom of the column through the return port 25

Structure of jacket: provided to the entire apparatus (not shown)

Pipe 4 that feeds the crystal-containing slurry 11a into the hydraulic wash column 1, inner diameter: 25 mm; one pipe Inner diameter of the melt loop line (discharging port 20, discharging line 21, product discharging line 23, return line 24, return port 25) such as a crystal discharging line: 25 mm Melting unit 22: double pipe heat exchanger A flow control valve (not shown) was installed in the product discharging line 23 in the melt loop.

Method for Operating Purification Apparatus

The purification apparatus was operated in the following way.

A slurry containing a mother liquor having a concentration shown in Table 1 below and acrylic acid crystals (feed slurry) was fed to the hydraulic wash column prepared under the conditions of a slurry concentration (crystal concentration) of 10% by mass, a slurry temperature of 10.5° C., and a flow rate of 220 kg/h. The internal pressure of the hydraulic wash column during operation was set at 0.4 MPa, and the rotation speed of the scraper at the bottom of the column was set at 30 rpm. A heating medium was introduced into the jacket.

The crystals were discharged together with the circulation liquid through the discharging port 20 of the hydraulic wash column 1 with a scraper at the bottom of the column and were sent as a circulation slurry to a heater (double pipe heat exchanger), which was a melting unit, at a flow rate of 220 kg/h.

The temperature of the heating medium in the double pipe heat exchanger was set at 30° C. The temperature of the liquid (circulation liquid) at the outlet of the heater was 20° C. While a portion of the circulation liquid was discharged as a product through the product discharging line 23, the rest of the circulation liquid was returned to the hydraulic wash column at the return percentage shown in Table 1. The return percentage refers to the percentage of the amount of the washing liquid for crystals relative to 100% by mass of the melt of the discharged crystals at which the circulation liquid containing the melt obtained in the melting step is returned to the hydraulic wash column.

The mother liquor in an amount corresponding to the difference between the amount of the crystal-containing slurry (feed slurry) and the amount of the product discharged through the product discharging line 23 was discharged from the hydraulic wash column through the mother liquor discharging pipe.

Measurement of Separation Efficiency

A high-performance liquid chromatograph and a gas chromatograph were used to measure the concentration of acrylic acid (AA) as well as the concentrations of acetic acid and furfural as impurities in the product and in the mother liquor in the feed slurry. The separation efficiencies of acetic acid and furfural were determined using the following equations.

Equations $$\text{(Acetic acid separation efficiency)} = \text{(Concentration of acetic acid in mother liquor in feed slurry)} / \text{(Concentration of acetic acid in product)}$$

$$\text{(Furfural separation efficiency)} = \text{(Concentration of furfural in mother liquor in feed slurry)} / \text{(Concentration of furfural in product)}$$

These separation efficiencies represent resistance to inclusion of acetic acid and furfural into crystals. The larger the values, the better the separation efficiencies.

Example 1

Acrylic acid was obtained as a product using the purification apparatus and its operation method described above, with the jacket inlet temperature being set at 23° C. Table 1 shows the concentrations of acetic acid and furfural in the product, and the separation efficiencies of acetic acid and furfural.

Example 2

Acrylic acid was obtained as a product as in Example 1, except that the concentration in the mother liquor in the feed slurry and the return percentage were changed as shown in Table 1. Table 1 shows the concentrations of acetic acid and furfural in the product, and the separation efficiencies of acetic acid and furfural.

Examples 3 and 4

Acrylic acid was obtained as a product as in Example 1, except that the concentration in the mother liquor in the feed slurry and the return percentage were changed as shown in Table 1 and that the jacket inlet temperature was set at 24° C. Table 1 shows the concentrations of acetic acid and furfural in the product, and the separation efficiencies of acetic acid and furfural.

Example 5

Acrylic acid was obtained as a product as in Example 1, except that the concentration in the mother liquor in the feed slurry and the return percentage were changed as shown in Table 1 and that the jacket inlet temperature was set at 25° C. Table 1 shows the concentrations of acetic acid and furfural in the product, and the separation efficiencies of acetic acid and furfural.

Example 6

Acrylic acid was obtained as a product as in Example 1, except that the concentration in the mother liquor in the feed slurry and the return percentage were changed as shown in Table 1 and that the jacket inlet temperature was set at 27° C. Table 1 shows the concentrations of acetic acid and furfural in the product, and the separation efficiencies of acetic acid and furfural.

Comparative Example 1

Acrylic acid was obtained as a product as in Example 1, except that the concentration in the mother liquor in the feed slurry and the return percentage were changed as shown in Table 1. Table 1 shows the concentrations of acetic acid and furfural in the product, and the separation efficiencies of acetic acid and furfural.

Comparative Example 2

Acrylic acid was obtained as a product as in Example 1, except that the concentration in the mother liquor in the feed slurry and the return percentage were changed as shown in Table 1 and that the jacket inlet temperature was set at 24° C. Table 1 shows the concentrations of acetic acid and furfural in the product, and the separation efficiencies of acetic acid and furfural.

Comparative Example 3

Acrylic acid was obtained as a product as in Example 1, except that the concentration in the mother liquor in the feed slurry and the return percentage were changed as shown in Table 1. Table 1 shows the concentrations of acetic acid and furfural in the product, and the separation efficiencies of acetic acid and furfural.

Comparative Example 4

Acrylic acid was obtained as a product as in Example 1, except that the concentration in the mother liquor in the feed slurry and the return percentage were changed as shown in Table 1 and that the jacket inlet temperature was set at 24° C. Table 1 shows the concentrations of acetic acid and furfural in the product, and the separation efficiencies of acetic acid and furfural.

TABLE 1

|  | Return percentage | Concentration in mother liquor ( %) | | | Concentration in product (ppm) | | Separation efficiency | |
|---|---|---|---|---|---|---|---|---|
|  |  | Acetic acid | Furfural | AA | Acetic acid | Furfural | Acetic acid | Furfural |
| Example 1 | 31% | 0.30 | 0.20 | 98.0 | 340 | 0.28 | 8.8 | 7118 |
| Comparative Example 1 | 30% | 0.19 | 0.28 | 99.5 | 271 | 1.45 | 7.0 | 1931 |
| Comparative Example 2 | 30% | 1.0 | 0.28 | 97.2 | 1177 | 0.63 | 8.1 | 4476 |
| Comparative Example 3 | 29% | 0.19 | 0.27 | 98.9 | 221 | 0.90 | 8.6 | 3000 |
| Example 2 | 32% | 0.32 | 0.21 | 98.0 | 362 | 0.29 | 8.9 | 7194 |
| Example 3 | 35% | 0.40 | 0.20 | 97.9 | 449 | 0.27 | 8.9 | 7407 |
| Example 4 | 40% | 0.60 | 0.19 | 97.7 | 663 | 0.24 | 9.1 | 7947 |
| Example 5 | 60% | 3.0 | 0.28 | 95.2 | 2929 | 0.15 | 10.2 | 18467 |
| Example 6 | 70% | 3.0 | 0.27 | 93.2 | 2388 | 0.07 | 12.4 | 39143 |
| Comparative Example 4 | 30% | 3.0 | 0.27 | 93.2 | 4743 | 90.4 | 6.2 | 30 |

The results in Table 1 demonstrate that excellent impurity separation efficiency can be achieved and a product can be efficiently obtained by a method for producing a compound including: a step of feeding a slurry containing crystals of the compound to a hydraulic wash column; a step of melting crystals in a crystal-containing circulation slurry discharged from the hydraulic wash column; and a step of returning a portion of a circulation liquid containing a melt obtained in the melting step to the hydraulic wash column, wherein the circulation liquid returned in the returning step in an amount of more than 30% by mass relative to 100% by mass of the melt serves as a washing liquid for crystals.

REFERENCE SIGNS LIST 1 hydraulic wash column
2 filter that filters crystal-containing slurry in hydraulic wash column
3 pipe that is connected to filter and discharges mother liquor
4 pipe that feeds crystal-containing slurry to hydraulic wash column
11 feed line (that feeds crystal-containing slurry to hydraulic wash column)
11a crystal-containing slurry
12 mother liquor
20 circulation slurry discharging port
21 discharging line that connects circulation slurry discharging port and melting unit
22 melting unit
23 product discharging line (connected to product discharging port)
23a (purified) product
24 return line (that connects melting unit and return port)
25 return port (for circulation liquid containing melt of discharged crystals)
P pump

The invention claimed is:

1. A method for producing a compound, the method comprising:
    a step of feeding a slurry containing crystals of the compound to a hydraulic wash column;
    a step of melting crystals in a crystal-containing circulation slurry discharged from the hydraulic wash column; and
    a step of returning a portion of a circulation liquid containing a melt obtained in the melting step to the hydraulic wash column through a return port of the hydraulic wash column, wherein the return port is provided at a bottom of the hydraulic wash column so that the circulation liquid is returned upward,
    wherein the circulation liquid returned in the returning step in an amount of more than 30% by mass relative to 100% by mass of the melt serves as a washing liquid for crystals.

2. The method for producing a compound according to claim 1,
    wherein the slurry to be fed to the hydraulic wash column contains a mother liquor, and the compound in the mother liquor has a purity of 97% by mass or less.

3. The method for producing a compound according to claim 1,
    wherein an outer wall surface of the hydraulic wash column is heated.

4. The method for producing a compound according to claim 3,
    wherein the outer wall surface of the hydraulic wash column is heated by a heating medium having a temperature at least 3° C. higher than the melting point of the compound.

5. The method for producing a compound according to claim 1, further comprising:
    a step of discharging a mother liquor, the step including filtering the crystal-containing slurry in the hydraulic wash column with a filter and discharging the mother liquor through a pipe connected to the filter,
    wherein a thermal conductivity of the filter is different from a thermal conductivity of the pipe.

6. The method for producing a compound according to claim 1, further comprising:
    a step of preparing the slurry containing crystals of the compound from a compound-containing solution.

7. The method for producing a compound according to claim 6,
    wherein the compound-containing solution is a (meth) acrylic acid aqueous solution or a crude (meth)acrylic acid solution.

8. The method for producing a compound according to claim 1, further comprising:
    a step of preparing the compound-containing solution from a raw material.

9. The method for producing a compound according to claim 8,
    wherein the raw material is at least one selected from the group consisting of propane, propylene, acrolein, isobutene, methacrolein, acetic acid, lactic acid, isopropanol, 1,3-propanediol, glycerol, and 3-hydroxypropionic acid.

10. A purification apparatus that purifies crystals, the purification apparatus comprising:
    a hydraulic wash column that includes a discharging port for a crystal-containing circulation slurry and a return port for a circulation liquid containing a melt of discharged crystals;
    a pipe that feeds a crystal-containing slurry to the hydraulic wash column;
    a filter that filters the crystal-containing slurry in the hydraulic wash column;
    a pipe that is connected to the filter and discharges a mother liquor;
    a unit that melts crystals in a circulation slurry discharged through the discharging port;
    a mechanism that returns a portion of a circulation liquid containing a melt obtained in the unit that melts crystals to the hydraulic wash column so that at least a portion of the returned circulation liquid serves as a washing liquid for crystals;
    a mechanism that controls an amount of the circulation liquid to be returned, wherein the return port is provided at the bottom of the hydraulic wash column so that the circulation liquid is returned upward, and
    wherein a thermal conductivity of the filter is different from a thermal conductivity of the pipe that is connected to the filter and discharges a mother liquor.

11. The purification apparatus according to claim 10, further comprising a mechanism that heats an outer wall surface of the hydraulic wash column.

12. The purification apparatus according to claim 10,
    wherein a ratio of the thermal conductivity of the pipe that is connected to the filter and discharges a mother liquor to the thermal conductivity of the filter is 10 to 100.

* * * * *